(12) United States Patent
Shull et al.

(10) Patent No.: US 7,083,939 B2
(45) Date of Patent: Aug. 1, 2006

(54) METHOD FOR DETERMINING CONCENTRATION OF CREATININE IN A BODILY FLUID

(75) Inventors: Bruce Shull, Indianapolis, IN (US); Alexandra N. Muchnik, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 288 days.

(21) Appl. No.: 10/426,236

(22) Filed: Apr. 30, 2003

(65) Prior Publication Data

US 2004/0126833 A1    Jul. 1, 2004

Related U.S. Application Data

(60) Provisional application No. 60/376,695, filed on May 1, 2002.

(51) Int. Cl.
*C12Q 1/34* (2006.01)

(52) U.S. Cl. ......................................................... 435/18
(58) Field of Classification Search ................... 435/18
See application file for complete search history.

(56) References Cited

U.S. PATENT DOCUMENTS

| | | | |
|---|---|---|---|
| 3,411,887 A | 11/1968 | Ku | |
| 4,816,393 A | 3/1989 | Siedel et al. | |
| 5,374,546 A | 12/1994 | Nagel et al. | |
| 5,436,133 A | 7/1995 | Fujita et al. | |
| 5,597,532 A | 1/1997 | Connolly | |
| 5,916,761 A * | 6/1999 | Koga et al. | 435/21 |
| 5,972,294 A | 10/1999 | Smith et al. | |

OTHER PUBLICATIONS

Carstesen et al., "Development and Evaluation of a Reagent Carrier with a new Reaction Sequence for the Determination of Creatinine in Blood, Plasma, Serum and Urine", Eur. J. Chem. Clin. Biochem. 1993, Vol. 31, No. 5, (12 pages).

Ogawa et al., "A New Enzymic Method for the Measurement of Creatinine Involving a Novel ATP-dependent Enzyme, N-Methylhydantoin Amidohydrolase", Biosci. Biotech.Biochem. 1995, vol. 59, No. 12, (3 pages).

Siedel et al., "Fully Enzymic Colorimetric Assay of Serum and Urine Creatinine which Obviates the Need for Sample Blank Measurements", Anal. Lett. 1988, vol. 21, No. 6, (9 pages).

Anonymous, "Entry of N-methylhydantoinase (AIP-hydrolysing) (EC-No. 3.5.2.14)", Brenda The Comprehensive Enzyme Information System. Online, XP002341620.

* cited by examiner

*Primary Examiner*—Ralph Gitomer
(74) *Attorney, Agent, or Firm*—Patton Boggs LLP (57) ABSTRACT

A method for determining concentration of creatinine in whole blood or plasma using a 1-methylhydantoinase (NM-Hase) catalyzed reaction, wherein the invention uses commercially available NMHase and thus eliminates prior art stabilization procedures for NMHase. Conveniently, known Trinder reagents and oxidative couplers are used for the indicator system. It has been found that by judiciously selecting the reagents used for the indicator system and/or varying the amount of enzyme NMHase that is loaded into the assay; the effect of the blank reaction can be minimized in the dynamic range of interest such that concentration of creatinine in normal and pathological levels can be measured directly without having to adjust for a blank reaction caused by bound N-methylhydantoin(NMH).

13 Claims, 5 Drawing Sheets

METHOD FOR DETERMINING CONCENTRATION OF CREATININE IN A BODILY FLUID

CROSS REFERENCE TO RELATED APPLICATIONS

This application claims priority to U.S. Provisional Patent Application Serial No. 60/376,695, filed May 1, 2002.

FIELD OF THE INVENTION

The present invention relates generally to methods and test apparatus for determining concentration of analytes such as creatinine in whole blood or plasma.

BACKGROUND

Creatine ($C_4H_9O_2N_3$ or $\alpha$-methyl guanidine-acetic acid) is a compound present in vertebrate muscle tissue, principally as phosphocreatine. Creatine is synthesized primarily in the liver and also in the pancreas and the kidneys. Creatine helps produce energy needed to contract muscles and it is produced at a relatively constant rate. Creatine is eventually spontaneously degraded into creatinine by muscle and is released into the blood. It is then excreted by the kidneys and removed by the body by glomerular filtration.

The amount of creatinine produced is relatively stable in a given person. Serum creatinine level is therefore determined by the rate it is being removed, which is roughly a measure of kidney function. If kidney function falls, serum creatinine level will rise. Thus, blood levels of creatinine are a good measure of renal function. Usually, increased creatinine levels do not appear unless significant renal impairment exists. Tietz N W, *Fundamentals of Clinical Chemistry*, $2^{nd}$ Edition, W B Saunders Company, 1982, pg. 994–995.

According to the American Diabetes Association (ADA), 20%–30% of patients with diabetes develop diabetic kidney disease (nephropathy). Further, some authorities recommend measurement of serum creatinine levels in non-diabetic patients to screen for renal dysfunction because of increasing evidence that dietary protein restriction and use of angiotensin-converting enzyme (ACE) inhibitors can retard progression once renal insufficiency develops. Thus, the need for creatinine testing as a measure of kidney function is well established.

Most methods for measuring creatinine levels are based upon the "Jaffe reaction" (1886), named after the German biochemist Max Jaffe (1841–1911), who discovered the reaction between creatinine and picrate ion in an alkaline medium that results in the formation of an orange-red complex. In 1904, Otto Folin adapted this method for use with urine. Folin, O. *Physiol Chem.* 1904, 41:223.

Several enzymatic methods are known for determination of creatinine in serum or urine, but they suffer from the disadvantage that they either proceed via creatine or ammonia as intermediate products in the reaction sequence. Since these substances are present in the serum or urine sample to be analyzed in concentrations which are quite substantial relative to creatinine, it is necessary to carry out differential measurements on two separate or successive reaction mixtures, the first of which the free creatine or ammonia is determined and the second of which the portion of additional creatine or ammonia formed from creatinine is determined. Such methods are relatively complicated for manual procedures and their application to automated analytical systems is also very limited, particularly when longer incubation periods are necessary for the completion of the conversion reactions.

U.S. Pat. No. 4,816,393 (Roche) discloses an enzymatic method for the determination of creatinine or 1-methylhydantoin. The substance 1-methylhydantoin is hydrolyzed to N-carbamoylsarcosine using the enzyme disclosed in the '393 patent, 1-methylhydantoinase (NMHase), which requires a nucleoside triphosphate, preferably ATP, as well as divalent metal ions and in some circumstances $K^+$ ions and/or $NH_4$ ions for its activity. Significantly, by using NMHase, a reaction pathway is provided, as shown below, that does not involve any intermediates found in appreciable concentrations in human blood.

Steps 3–5 of the above reaction pathway are disclosed in U.S. Pat. No. 4,645,739 (Roche), wherein a process for making the enzyme N-carbamoylsarcosine-amidohydrolase (CSHase) is disclosed. A corresponding photometric method for the determination of creatinine is also described in J. Siedel et al., *Anal. Letters* 21, 1009–1017 (1988). Endogenous substances present in body fluids should not interfere with this creatinine or 1-methylhydantoin determination since 1-methylhydantoin and the reaction products of the subsequent indicator reaction are not natural components of serum or urine. Therefore, a sample blank measurement should not be necessary.

Unfortunately, however, commercially available NMHase, which is needed to catalyze the reaction, requires enzyme-bound 1-methylhydantoin (NMH) for its stability. That is, NMHase is stabilized by its own substrate. According to U.S. Pat. No. 5,374,546 (Roche), in the presence of a nucleoside triphosphate and divalent metal ions, such as $Mg^{2+}$, the NMH is completely degraded enzymatically and causes a blank reaction similar to an endogenous substrate. According to the '546 patent, "since the blank reaction caused by enzyme-bound NMH depends on the one hand on the amount of NMHase used and on the other hand also on the varying NMH content of the NMHase itself, it is also necessary to always determine the blank reaction separately for such a test and this blank value has to be subtracted from the measured value." '546 patent, column 2, lines 65–68 (emphasis added). The '546 patent discloses a method for stabilizing NMHase after the NMH substrate has been removed. According to the '546 patent, NMH can be removed, the stabilization procedure for NMHase employed, and creatinine concentration can be tested using the reaction pathway shown above, without requiring a blank reaction.

Figure 1:
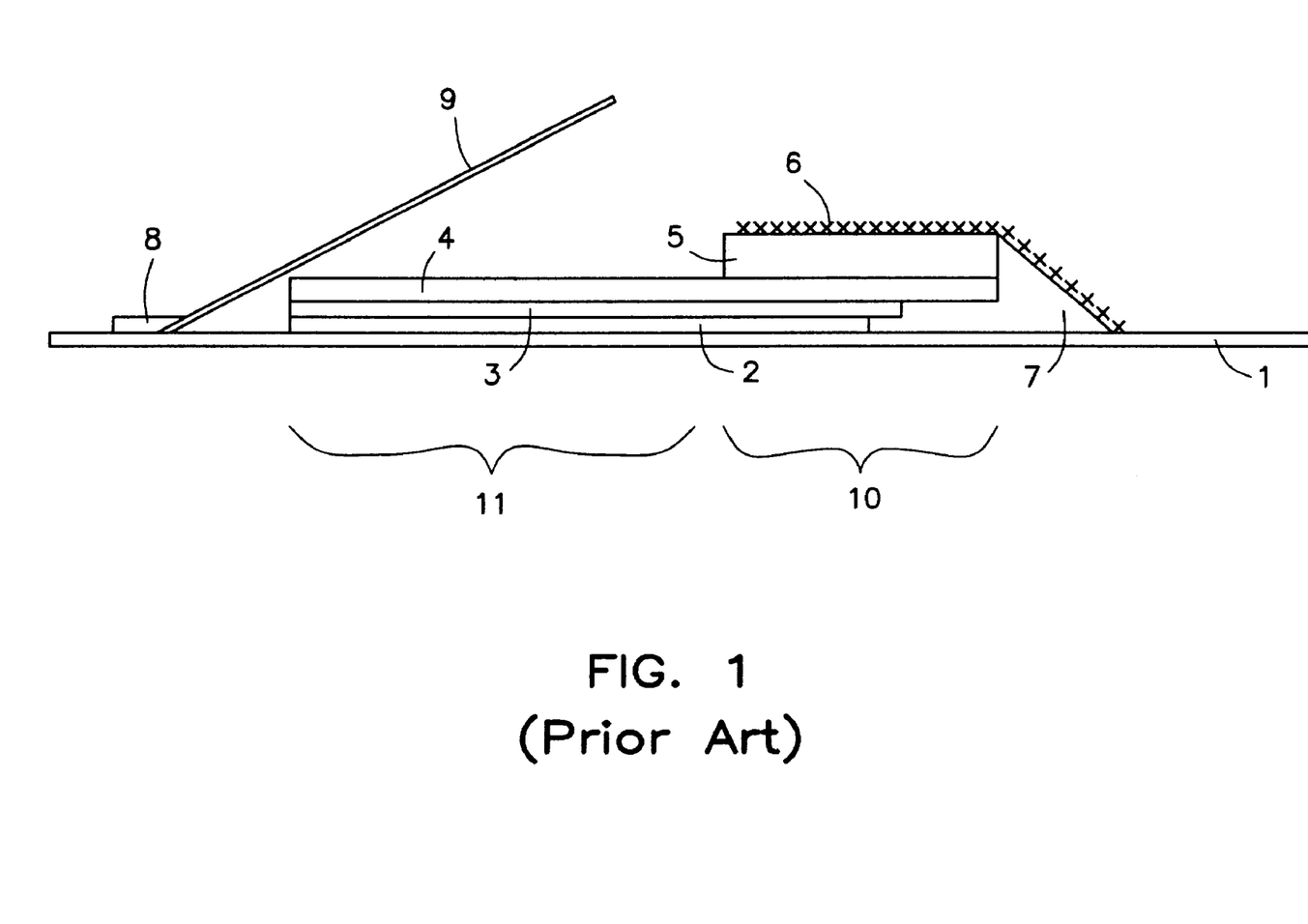
FIG. 1 is a side sectional view of a prior art creatinine test strip as taught by U.S. Pat. No. 5,374,546.

With reference to FIG. 1, the prior art creatinine measuring device of the '546 patent includes supporting layer 1, layers 2 and 3 which are impregnated with components of the reagent system, a transport layer 4 preferably made of glass fibers, and blood separation layer 5, also preferably made of glass fibers. In use, 30 µl of blood is applied to layers 6 and 5. The sample seeps into transport layer 4 where red blood cells are separated during tangential (right to left) fluid migration. A reaction takes place in layers 2 and 3 between the constituents of the sample which is to be determined and the reagents impregnated in the layers 2 and 3. At a predetermined time after applying the sample, the indicator reaction is determined photometrically.

The stabilized NMHase is impregnated in layer 2 along with ATP, $MgCl_2$, and a complexing agent (EDTA) that complexes the metal ions which are necessary to stabilize the NMHase. The indicator, a "Julolidino" indicator whose preparation is described in U.S. Pat. No. 4,665,023, is impregnated into layer 3, along with additional $MgCl_2$ and $NH_4Cl$.

Unfortunately, the inventors of the present invention have found two major drawbacks with the stabilization procedure disclosed in the '546 patent. First, they found it difficult to accomplish. Second, the "Julolidino" indicator disclosed in the patent is not commercially available. The '023 patent suggests that creatinine and uric acid assays are especially prone to interferences and require improved indicators, such as the Julolidino indicators. Further, a Reflotron Uric Acid bulletin applicants have reviewed states "Boehringer Mannheim has improved upon this procedure by including a special indicator, allowing evaluation of the reaction by reflectance photometry." At any rate, the applicants of the present invention were influenced by the literature just mentioned, and feared that efforts to create a creatinine test assay would fail without using the Julolidino indicators and stabilization procedures taught by the prior art.

It would be desirable to have a creatinine test assay using NMHase that avoids the elaborate stabilization procedure and that uses conventional, off-the-shelf chromogens.

SUMMARY OF THE INVENTION

The present invention provides an apparatus and method for determining concentration of creatinine in whole blood or plasma, characterized in that NMHase having its NMH substrate bound thereto is used in the test without having to separately determine and adjust for a blank reaction. Thus, the present invention eliminates the complicated stabilization procedures for NMHase that the prior art teaches are always necessary. Furthermore, the present invention utilizes known and readily available Trinder pairs for color production. The chromogens and their coupling reagents are judiciously selected and/or the amount of NMHase used in the test assay is carefully predetermined such that color production corresponds to the concentration of analyte being measured and is substantially unaffected by the blank reactions in the concentration range of interest.

In one form thereof, the present invention provides a test strip for determining concentration of creatinine in a body fluid sample. The test strip comprises a reagent layer impregnated with 1-methylhydantoinase ("NMHase") having 1-methylhydantoin ("NMH") bound thereto. When wetted with sample, the test strip produces a colored response that is substantially proportional to the concentration of creatinine over its normal and at least part of its pathological range. That is, the colored response is substantially unaffected by a blank reaction.

To understand the advantages of the present invention, one must understand that commercially available NMHase (Roche Diagnostics) has NMH substrate bound thereto for stability. The NMH substrate can be removed, but shelf life of the NMHase so produced is very short, and this NMHase is thus unsuitable for creating a test assay. On the other hand, as noted above, the prior art teaches that using NMHase having its substrate NMH bound thereto in a test assay, while stable, always requires determining the blank reaction separately, and the blank value has to be subtracted from the measured value. See U.S. Pat. No. 5,374,546, column 2, lines 65–68. To avoid having to conduct a separate test to adjust for the blank reaction, the prior art teaches what the applicants have found to be an elaborate, costly and difficult stabilization procedure for NMHase.

In direct contradiction of the teachings of the prior art, the inventors of the present invention have found, quite remarkably and surprisingly, that bound NMHase can be used in an NMHase-catalyzed creatinine assay without having to adjust for a blank reaction. This remarkable result is achieved by judiciously selecting the Trinder chromogen and coupling reagent indicator system and/or carefully predetermining the amount of NMHase (having substrate bound thereto) that is used to impregnate the reaction membrane of the test strip.

Without wishing to be tied to any specific theory, applicants speculate that certain, select Trinder reagents may require a threshold level of $H_2O_2$ below which no color is produced. In such case, the NMH substrate produces a small amount of $H_2O_2$, but the $H_2O_2$ in turn produces no color with the Trinder reagent. Such a phenomenon could be attributed to the redox potential of a given Trinder reagent. Under such a theory, one could select the Trinder reagent such that the "threshold level," as it were, corresponds with the concentration of bound NMH, such that color production begins essentially with the concentration of creatinine desired to be measured.

A related theory to explain the applicants' amazing innovation is that certain Trinder reagents are not sufficiently selective to react with all of the $H_2O_2$ that is produced during the assay. Under such theory, a small amount of $H_2O_2$ is instead expended in "side-reactions," the remainder reacting with the Trinder reagents to produce color. For example, $H_2O_2$ may undergo auto-oxidation, forming water and oxygen spontaneously instead of reacting with the Trinder system to produce color. $H_2O_2$ is quite reactive and can undergo any number of other "side reactions" as opposed to reacting with the Trinder reagents to produce color. Under this theory, the Trinder reagents are selected such that the side reactions consume just enough $H_2O_2$ to correspond with the bound NMH. The remaining $H_2O_2$ produces a colored test response that corresponds to the amount of creatinine in the test sample.

Whatever the mechanism for applicants' invention may be, applicants have proven empirically in the examples presented hereinbelow that by judiciously choosing a Trinder reagent and/or carefully predetermining the amount of NMHase used in the test assay, creatinine concentration can be measured as a function of color production over a sufficiently wide range of normal and pathological creatinine concentrations—without having to account for a blank reaction. Applicants' inventive method and test assay represent a major and remarkable breakthrough in dry-phase testing of creatinine using an NMHase-catalyzed reaction.

One significant advantage of the present invention is that it avoids the procedure taught by the prior art to stabilize the NMHase having its bound substrate removed, which procedure applicants have found to be costly and difficult to reproduce. Instead, with the present invention, NMHase having NMH bound thereto can be used without having to adjust the result for a blank reaction. The blank reaction, to the extent a blank reaction occurs, does not significantly interfere with the direct correlation between color produced and concentration of analyte over the concentration range of interest.

Another advantage of the present invention is that it does not require special chromogens. Instead, the present invention can be used with ordinary and readily available Trinder reagents and oxidative couplers.

BRIEF DESCRIPTION OF DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 2:
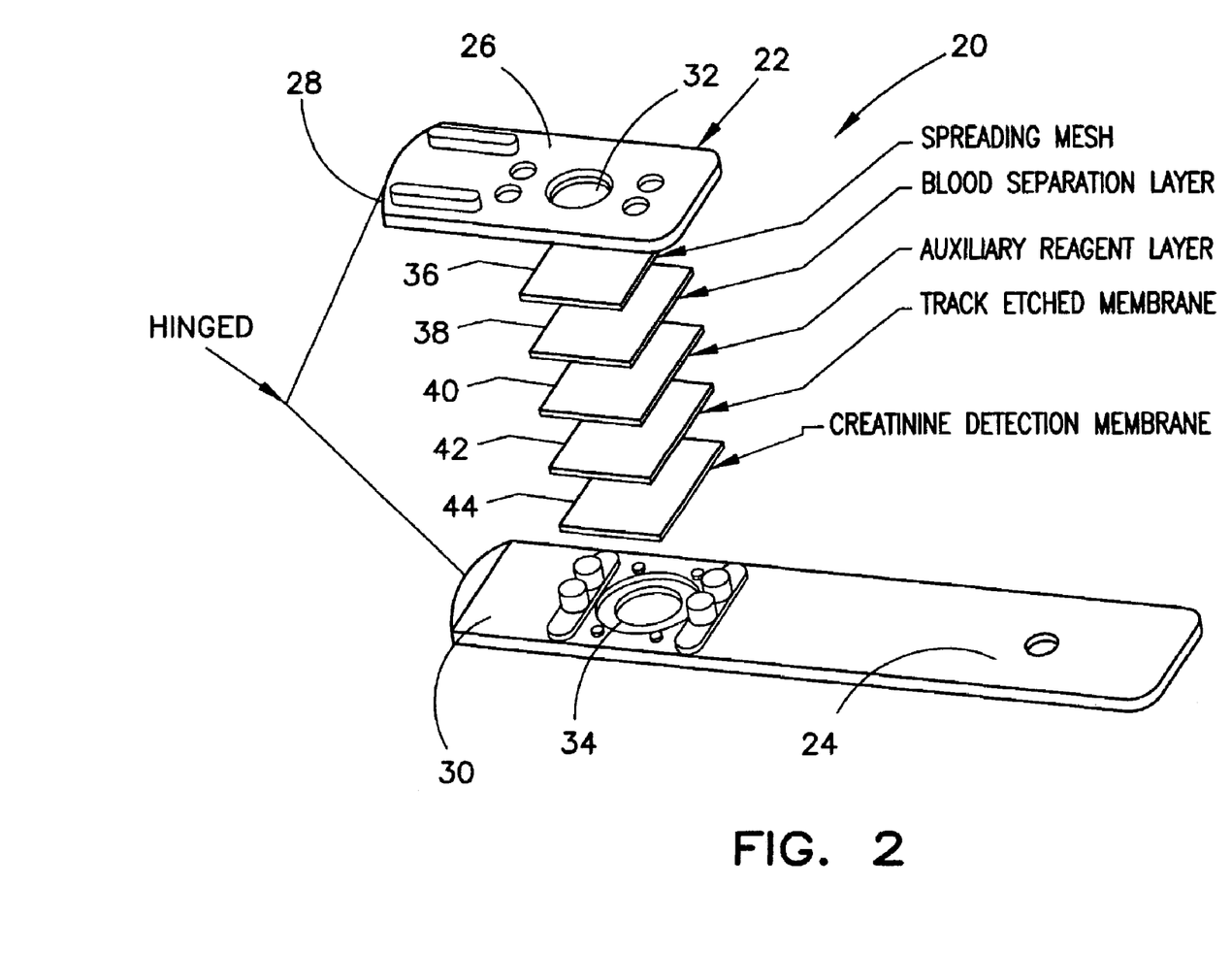
FIG. 2 is an exploded perspective view of a test strip used to measure creatinine in accordance with the present invention.

Referring now to FIG. 2, test strip 20 includes test strip holder 22 which is preferably formed by injection molding. Test strip holder includes handle 24 and end portion 26 which is preferably hingedly attached by hinge portion 28 to second end portion 30, shown exploded away in FIG. 2. Portion 26 is foldable about hinge portion 28 over portion 30 as shown. End portion 26 includes an opening 32 while end portion 30 includes a complementary spaced opening 34. When end portion 26 is folded over end portion 30, openings 32 and 34 are aligned. In its folded position, opening 32 in holder 22 defines an area for depositing a body fluid sample while opening 34 defines an area in which optoelectronic measurements of chemistry test reactions are conducted.

The test strip holder is not critical to the invention and other suitable embodiments of a test strip holder are contemplated by this invention. The particular test strip described herein is suitable for use with an optoelectronic instrument sold under the trademark BIOSCANNER, commercially available from Polymer Technology Systems, Inc., Indianapolis, Ind.

Returning to FIG. 2, there are five layers held within test strip holder 22 without requiring adhesives. It has been found that it is desirable to exert a compressive force upon the layers between end portion 26 and end portion 30. A desirable compressive force to be exerted on the test layers by the test strip reduces the height of the stack of layers by about twenty percent (20%) from the height the layers would occupy if no compressive force were exerted. It is believed that compressing the layers removes air pockets within the test matrix and thereby improves the speed with which the physical and chemical processes take place. This, in turn, improves the precision of the test.

The top layer 36 is a disbursement or spreader mesh layer formed of, for example, woven materials such as polyester or cotton, non-woven fabric, gauze or monofilament yarn. One suitable material for spreader layer 36 is a Sefar PeCap (07-17/9) available from Sefar American, Inc., DePew, N.Y. Layer 36 provides rapid and even disbursement of a body fluid such as whole blood or plasma.

Beneath and in fluid communication with disbursement or spreader layer 36 is blood separation layer 38. The composition, preparation and function of blood separation layer 38 are described in greater detail in co-pending U.S. utility application Ser. No. 10/329,044, which uses the same blood separation layer. Application Ser. No. 10/329,044 is commonly owned by the assignee of the present application and is hereby incorporated herein by reference in its entirety. Blood separation layer 38 separates at least most of the red blood cells (erythrocytes) from plasma and passes the plasma therethrough, retaining (most) red blood cells. Blood separation layer 38 is generally a glass fiber membrane. A suitable commercial membrane for layer 38 is Ahlstrom Grade 144, thickness 0.378 mm, available from Ahlstrom Filtration, Inc., Mt. Holly Springs, Pa. Other glass fiber matrices could be substituted. Generally, layer 38 should include glass fibers with a diameter of 0.5 to 2 microns and a density of 0.1 to 0.5 $g/cm^3$, more preferably 0.1 to 0.2 $g/cm^3$. To improve effectiveness of blood cell separation, layer 38 is impregnated with a salt and sugar, examples and quantities of which are set forth in the examples hereinbelow.

Beneath and in fluid communication with blood separation layer 38 is a reagent matrix comprising at least two layers. In the illustrated embodiment, the three layers 40, 42 and 44 are the reagent matrix. The reagent matrix is in fluid communication with layer 38. The reagent matrix includes all of the reagents for the creatinine test assay.

The first layer of the reagent matrix is auxiliary reagent layer 40. Layer 40 is a filter paper made from cellulose acetate in one embodiment. One suitable membrane for layer 40 is paper grade 595, 0.180 mm (7.1 mil) thick, available from Schleicher & Schuell, Keene, N.H. CytoSep® grade 1660 membrane, 12.9 mils thick, available from Pall Specialty Materials, Port Washington, N.Y. may also perform suitably as layer 40, although the shape of the standard curve would be changed. Layer 40 is impregnated with a nucleoside triphosphate, preferably ATP, a Trinder chromogen, a divalent salt, preferably $MgCl_2$ and ascorbate oxidase. ATP and $MgCl_2$ are placed in the auxiliary layer, apart from the NMHase, because NMHase shows ATPase activity and can degrade ATP over time. Layer 40 may retain residual red blood cells that escape layer 38 and pass into layer 40.

The chromogen pair must be kept separate for stability. If the chromogen pair is put in the same layer at high pH (around 8.0) there is rapid and spontaneous color formation.

Ascorbic acid is known to interfere in Trinder reactions; it causes decreased results. Ascorbate oxidase oxidizes ascorbate to produce water, and it therefore prevents interference from ascorbic acid without producing color. The ascorbate oxidase is loaded in the auxiliary reagent layer to mop up the ascorbic acid before the main creatinine reaction.

The $MgCl_2$ and ATP are kept separate from the NMHase to maintain stability of the NMHase. If ATP and Mg are in contact with the NMHase, the bound substrate is reacted and the enzyme rapidly loses activity.

As described in the examples below, the aqueous solution used to load the components into the auxiliary layer is mildly acidic, around pH 6.0, which has been found to stabilize ATP. It is also needed to prevent spontaneous color formation from the Trinder pair as noted above. Regarding pH of the two reaction compartments, it should be noted that the auxiliary reagent compartment (layer 40) is at a much lower buffer concentration than the main reagent compartment (compare: auxiliary layer 40 at 20 mM vs. main layer 44 at 100 mM). This is to ensure that the final pH is determined by the buffer in the final reaction compartment (layer 44) and that this final pH is optimum for the creatinine reaction pathway.

Layer 42 is a polycarbonate track etched membrane having uniform cylindrical pores. Track etching is a process in which PCTE is first bombarded by a neutron beam. After bombardment, the material is treated with acid which etches holes where the neutrons have struck. This technology is used to create very uniform holes or pores. A commercially available layer 42 is available from Osmonics, Poretics Standard PCTE, Catalogue # K04CPB; thickness 10 μM. The function of layer 42 is to improve uniformity of the color reaction.

Layer 44 is the main reagent-containing membrane or layer which includes the enzyme system for the creatinine assay. A membrane suitable for layer 44 is a nylon membrane available from Cuno Specialty Membrane Products under part number BLA 045. The solution used to impregnate layer 44 is slightly alkaline, which has been found to maximize the reactivity of the enzymes during the test.

The potassium and ammonium salts loaded into layer 44 are required for activity of the NMHase. If these salts are not included, the production of color is greatly decreased and a satisfactory reaction cannot be obtained. The EDTA may not be needed, and in applicants' embodiments, it is included at much lower concentration than the magnesium ions. There is no relation in applicants' embodiments to the stabilization procedure disclosed in the '546 patent. Applicants include EDTA as a precaution against low levels of heavy metal contamination, as is often done in enzyme formulations.

After the blood sample is contacted with disbursement layer 36 and the sample enters auxiliary layer 40, the chromogen loaded in layer 40 is fluidly transported to the bottom layer 44, and color is produced in layer 44, which is the main reaction layer. That is to say, once the strip is wetted with sample, the reagents migrate to bottom layer 44.

The following examples will enable one of ordinary skill in the art to fully practice the present invention. The examples illustrate the preparation of the various layers of the test matrix and the solutions that are used to impregnate the various test membranes or layers.

EXAMPLE 1

Blood Separation Membrane

Ahlstrom Grade 144, which is a glass fiber membrane with a thickness of 0.378 mm, was impregnated with an impregnation solution of the following composition:

| | |
|---|---|
| Water, D.I. Purified | 800 g |
| NaCl | 10 g |
| Sorbitol | 75 g |
| Citric Acid | 0.21 g |
| pH 4.2–4.4 | |

Q.S. to 1000 ml with D.I. Water

The membrane was immersed in a re-circulating bath of impregnation solution at a rate of 0.5 ft/min. The membrane was dried by passage through a tunnel with blowing warm air (98° to 106° F.) and low humidity (<5% RH).

EXAMPLE 2

Auxiliary Reagent Membrane

Schleicher and Schuell Grade 595 paper, which is a pressed paper with a thickness of 0.180 mm, was impregnated by immersion in the following solution:

| | |
|---|---|
| Sodium Phosphate Buffer, pH 6.0 | 20 mM |
| $Na_2ATP$ | 60 mM |
| N-Ethyl-N-(2-hydroxy-3-sulfopropyl)-3, 5-dimethylaniline (MAOS) | 57 mM |
| $MgCl_2$ | 5 mM |
| Ascorbate Oxidase | 150 U/ml |

Final Volume is 100 ml made with D.I Water

Impregnation was done manually and the excess liquid removed by lightly wiping with a rubber squeegee. The membrane was dried at 95°–105°F. in a tunnel with blowing air.

EXAMPLE 3

Creatinine Detection Membrane with 3-Methyl-2-Benzothiazolinone (MBTH)

A nylon membrane (Cuno Specialty Membrane Products, membrane BLA 045) was impregnated as in example 2 with an impregnation solution of the composition below. The N-methylHydantoinase (NMHase) used in the following solution was not stabilized and had its substrate, NMH bound thereto.

| | |
|---|---|
| TAPS Buffer, pH 8.0 | 100 mM |
| KCl | 200 mM |
| $NH_4Cl$ | 10 mM |
| EDTA $Na_2$ | 0.5 mM |
| Triton X100 | 0.3% |
| Bovine Serum Albumin (BSA) | 1% |
| Sucrose | 4.5% |
| Dextran Sulfate 500,000 M.W. | 0.75% |
| Creatinine Deiminase | 430 U/ml |
| N-MethylHydantoinase | 34 U/ml |
| Sarcosine Oxidase | 231 U/ml |
| Carbamoyl Sarcosine Hydrolyase | 92.4 U/ml |

-continued

| | |
|---|---|
| Peroxidase | 1400 U/ml |
| 3-Methyl-2-Benzothiazolinone (MBTH) | 1.8 mM |

Final Volume is 100 ml made with D.I. Water

The impregnated membrane was dried as in Example 2.

EXAMPLE 4

Creatinine Detection Membrane with 4-Aminoantipyrine (AAP)

A creatinine impregnation solution was prepared as in Example 3 except that (AAP) was substituted for MBTH as the coupling reagent. The solution was used to prepare a creatinine detection membrane as in Example 3 using a BLA 045 membrane.

EXAMPLE 5

Creatinine Detection Membrane with Varied NMHase Levels

Four Creatinine Detection Membranes were made using MBTH as the coupling reagent but the amount of NMHase in each solution was varied. The amounts of NMHase tested were 34, 17, 8.5, and 3.4 U/ml, respectively. The membranes used for all four membranes were again Cuno BLA 045. The impregnation solutions were made as in Example 3, the only difference being that the amount of NMHase was varied, as noted.

EXAMPLE 6

Test Strip Assembly

Place the membranes in the following order between the pins in the test strip holders: bottom layer is Creatinine Detection Membrane 44, then a polycarbonate track etched membrane 42 (Osmonics, Inc.), then Auxiliary Reagent Membrane 40, then Blood Separation Layer 38 and finally the Mesh Screen Layer 36. Fold the test strip portions 26 over portion 30 and press to ensure closure. Stake the strip holders 22 using a cold stake press, cut them to individual strips and place in vials with desiccant.

EXAMPLE 7

Assay of Creatinine in Blood Serum Using MBTH Based Creatinine Test Strips

Figure 3:
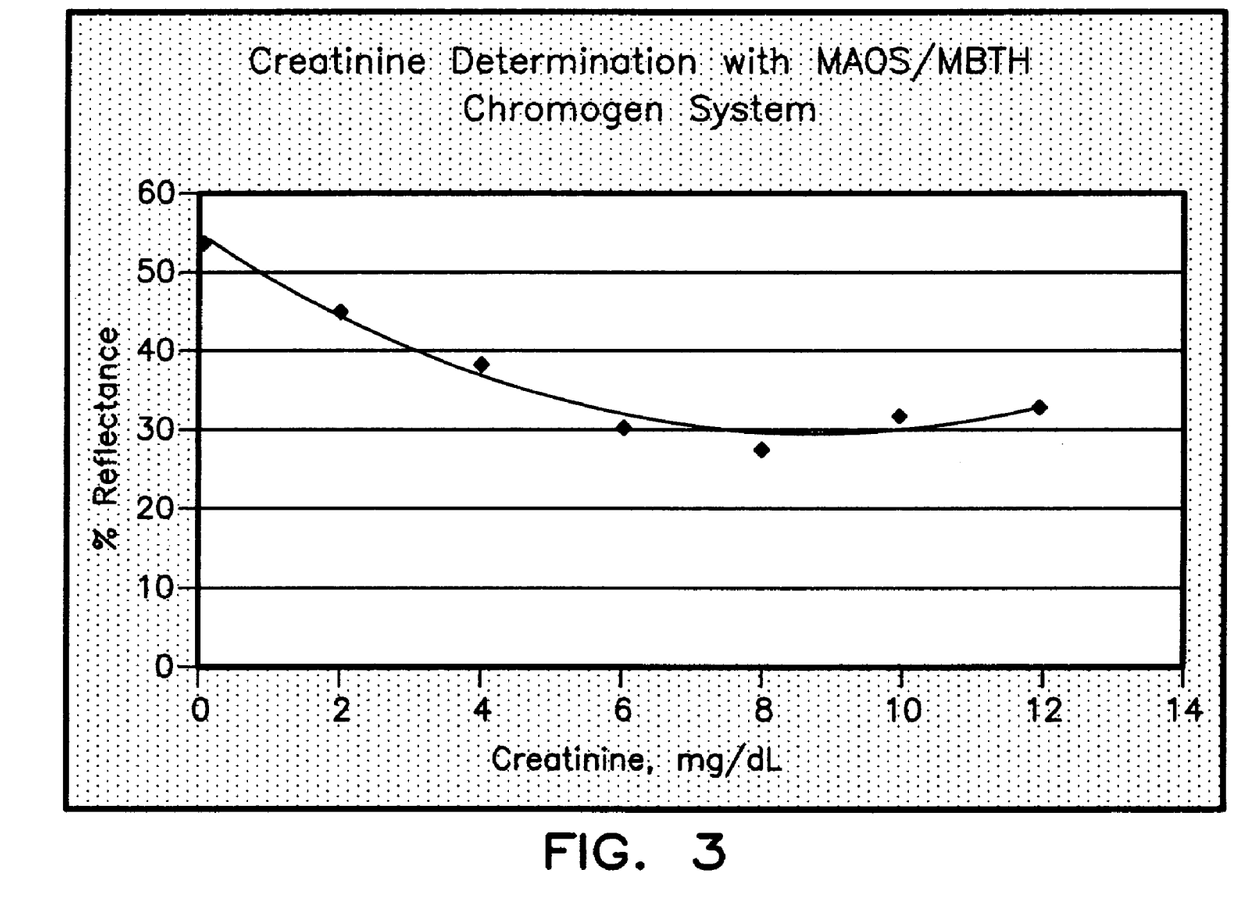
FIG. 3 is a graph of known creatinine concentration versus measured reflectance for a creatinine test strip in accordance with example 7 of this disclosure, wherein the Trinder reagent was MAOS and the coupling reagent was MBTH.

Test strips were assembled using membranes prepared in Examples 1, 2 and 3 and assembled according to Example 6. Commercially available Human Control Serum was used as the sample. The base value of this Control was 2.0 mg/dl Creatinine. Aqueous creatinine solution, 100 mg/dl in water, was used as a spike solution to achieve creatinine concentrations up to 12 mg/dl. Water was used as a blank sample. Percent Reflectance using a green LED was recorded at the reaction endpoint. Table I contains the data for Graph 1, which is presented in FIG. 3. Each data point is the mean of duplicate measurements.

TABLE 1

Creatinine Detection Membrane with MAOS/MBTH Chromogen System

| Creatinine Concentration, mg/dl | % Reflectance Green LED |
|---|---|
| 0 | 55.54 |
| 2 | 45.40 |
| 4 | 36.55 |
| 6 | 29.89 |
| 8 | 30.81 |
| 10 | 29.41 |
| 12 | 30.69 |

EXAMPLE 8

Assay of Creatinine in Blood Serum Using AAP Based Creatinine Test Strips

Test strips were assembled using membranes prepared in Examples 1, 2, and 4 and assembled according to Example 6. Commercially available Human Control Serum was used as the sample. The base value of this Control was 2.0 mg/dl Creatinine. Aqueous creatinine solution, 100 mg/dl in water, was used as a spike solution to achieve creatinine concentrations up to 12 mg/dl. Water was used as a blank sample. Percent Reflectance using a green LED was recorded at the reaction endpoint. Table 2 contains the data for Graph 2 which is presented in FIG. 4. Each data point is the mean of two (2) duplicate measurements.

TABLE 2

Creatinine Detection Membrane with MAOS/AAP Chromagen System

| Creatinine Concentration, mg/dl | % Reflectance Green LED |
|---|---|
| 0 | 87.69 |
| 2 | 82.19 |
| 4 | 69.36 |
| 6 | 60.03 |
| 8 | 54.46 |
| 10 | 48.72 |
| 12 | 42.79 |

EXAMPLE 9

Assay of Creatinine in Whole Blood Using MBTH and Varying Amounts of NMHase

Test strips were assembled using membranes prepared in Examples 1, 2 and 5 and assembled according to Example 6. A sample of whole blood anticoagulated with EDTA, with creatinine less than 1 mg/dl was used as the sample. Aqueous creatinine solution, 100 mg/dl in 0.85% saline, was used as a spike solution to achieve creatinine concentrations up to 10 mg/dl. Saline was added to dilute the plasma to achieve a creatinine of near 0. Two sets of samples were used in these experiments. See Table 3. Percent Reflectance using a green LED was recorded at the reaction endpoint. Table 3 contains the data for Graph 3 which is presented in FIG. 5. Each data point is the mean of five measurements.

TABLE 3

Creatinine Detection Membrane with MAOS/MBTH Chromagen System and varied NMHase

| Creatinine, mg/dl | % Reflectance 34 U/ml NMHase | Creatinine, mg/dl | % Reflectance 17 U/ml NMHase | % Reflectance 8.5 U/ml NMHase |
|---|---|---|---|---|
| 0.1 | 32.64 | 0.1 | 40.88 | 44.71 |
| 1.4 | 25.07 | 0.7 | 38.37 | 41.96 |
| 4.7 | 22.31 | 1.2 | 36.17 | 40.94 |
| 6.3 | 22.58 | 1.9 | 34.31 | 37.17 |
| 8.7 | 18.57 | 3.2 | 30.06 | 31.97 |
| 11.1 | 20.64 | 4.9 | 25.56 | 27.98 |
|  |  | 5.8 | 23.87 | 24.64 |
|  |  | 6.9 | 22.19 | 21.55 |
|  |  | 8.9 | 19.09 | 19.44 |
|  |  | 10.9 | 17.14 | 18.36 |

The standard curve gave optimum response at 8.5 U/ml NMHase using MAOS/MBTH as the chromogen system. At 3.4 U/ml NMHase, the amount of color formation dropped off sharply. For 3.4 U/ml, there was such a low response that only a couple of levels were run and testing was discontinued. At NMHase of 17 to 34 U, the standard curve became less sensitive, causing a loss of precision and dynamic range. From these results, it can be appreciated that the shape of the standard curve giving optimum performance depends critically on the amount of NMHase activity and the chromogen system.

Figure 4:
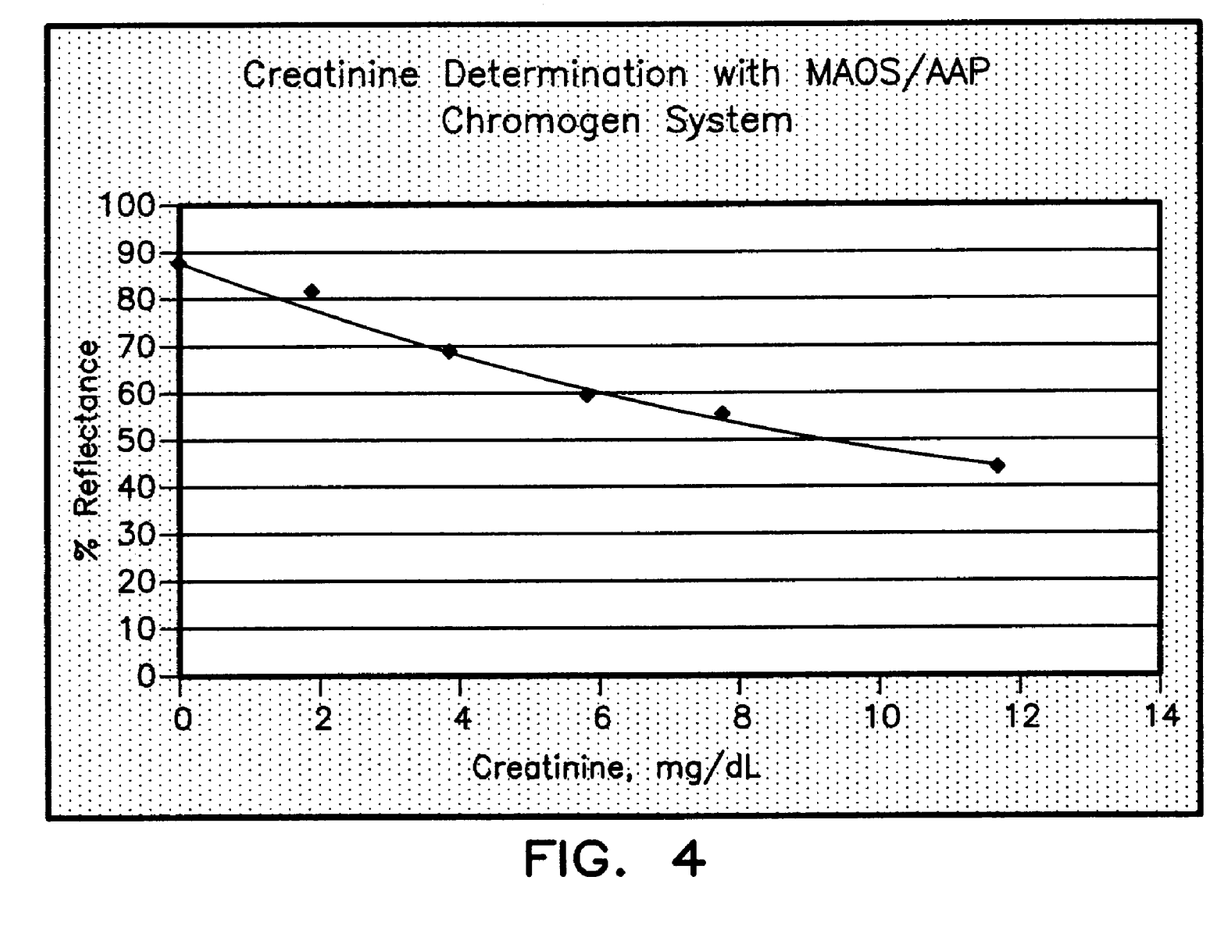
FIG. 4 is a graph of known creatinine concentration versus measured reflectance for a creatinine test strip in accordance with example 8 of this disclosure, wherein the Trinder reagent was MAOS and the coupling reagent was AAP.

With reference to FIG. 4, with less reactive Trinder coupling pairs such as MAOS/AAP there is a loss of sensitivity at creatinine levels less than 2 mg/dl, i.e., the standard curve is flat in this range. Without wishing to be tied to any specific theory, the flat response at lower creatinine concentration levels may be due to most of the bound NMH and even some of the creatinine being consumed by "side reactions" before the creatinine begins reacting with the Trinder indicator system to produce color. Whatever the reason for the lower sensitivity at low concentrations, such a system may nonetheless have applications where wider dynamic range is needed, such as the measurement of urine creatinine.

Figure 5:
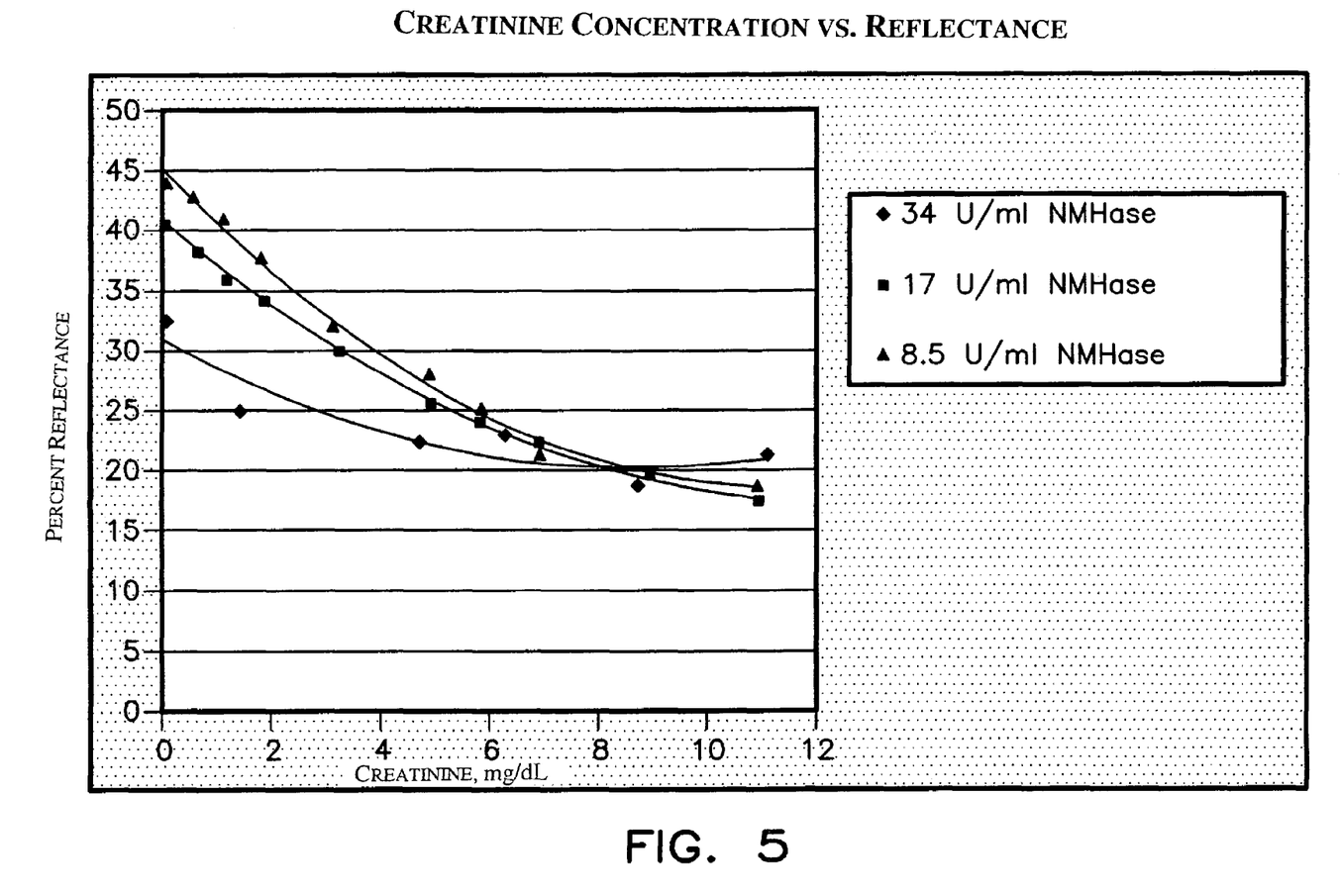
FIG. 5 is a graph of known creatinine concentration versus measured reflectance in accordance with example 9 of this disclosure, wherein the Trinder pair was MAOS/MBTH and the amount of bound NMHase impregnated into the test matrix was varied as indicated.

On the other hand, with a more reactive chromogen system such as MAOS/MBTH it is possible to balance the blank reaction attributable to bound NMHase by adjusting the amount of NMHase. With reference to FIG. 5, the standard curve drawn from the solid, diamond-shaped data points was generated from a test assay wherein NMHase was impregnated in layer 44 at 34U/ml, which is relatively high. At lower concentrations of creatinine in the test sample, percent reflectance is lower, and at higher concentrations, the curve is flat. This is attributable to the blank reaction of bound NMH producing color which interferes with color production from the creatinine present in the sample.

As shown with reference to the curves drawn from the square and triangular data points, 17 and 8.5 U/ml, respectively, with lower amounts of NMHase loaded into the test assay, interference from the blank reaction is reduced. The curves (especially 8.5 U/ml of NMHase—triangle points) are sensitive in the normal range of creatinine concentration (0–2 mg/dl) and in the pathological range up to at least 10 mg/dl. As can now be appreciated, by judiciously choosing the Trinder coupling pairs and/or carefully predetermining the amount of bound NMHase to be initially loaded into the test assay, a standard curve can be produced that is sensitive over a wide range of normal and pathological creatinine concentrations without interference from a blank reaction. It is thus unnecessary with the present invention to remove the stabilizing NMH and risk loss of enzyme activity during manufacturing steps. This greatly simplifies assay formulation and represents a significant breakthrough.

It is envisioned that a suitable creatinine test strip can be mass-produced using MAOS/MBTH with 8.5U/ml NMHase.

While the above disclosure is directed to determining concentration of creatinine using an NMHase-catalyzed reaction, the principles taught hereinabove can be applied to testing for other analytes. In a general sense, this application teaches a method of determining concentration of an analyte in a sample using an enzyme-catalyzed reaction in which an interfering substance is present to stabilize the enzyme. In accordance with the inventive method, an indicator is judiciously selected from a plurality of indicators in order to minimize color production by the blank reaction produced by the interfering substance during the reaction. Having judiciously selected a desirable indicator, the reaction is carried out and a colored response produced that is substantially proportional to the concentration of the analyte over its normal and at least part of its pathological range. In this manner, the colored response is substantially unaffected by the blank reaction. It may also be necessary, in addition to or in lieu of judiciously selecting an indicator, to predetermine the initial concentration of the enzyme and interfering substance in the assay which minimizes interference by the blank reaction. Preferably, in accordance with the above teachings, the reaction is carried out in one or more layers of a dry phase test strip. Of course, in the specific embodiment disclosed hereinabove, the enzyme is NMHase and the interfering substance is NMH.

While a preferred embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of determining concentration of creatinine in a sample using an enzyme-catalyzed reaction in which an interfering substance is present to stabilize the enzyme, said method comprising:

(a) selecting an indicator from a plurality of indicators to minimize color production by a blank reaction produced by the interfering substance during the reaction; and (b) producing a colored response that is substantially proportional to the concentration of creatinine over its normal and at least part of its pathological range; and (c) determining said concentration of creatinine in said sample from said colored response without subtracting a blank value associated with said blank reaction and without utilizing an additional reaction to suppress interference with said colored response.

2. The method of claim 1, further comprising determining the initial concentration of said enzyme and said interfering substance which minimizes said interference by said blank reaction.

3. The method of claim 1, wherein the reaction is carried out in one or more layers of a dry phase test strip.

4. The method of claim 1, wherein the enzyme is 1-methylhydantoinase (NMHase) and the interfering substance is N-methylhydantoin (NMH).

5. The method of claim 1, wherein the indicator comprises a Trinder pair.

6. A method of determining concentration of creatinme in a sample using a 1-methylhydantoinase (NMHase) catalyzed reaction, comprising: using 1-methylhycantoinase (NMHase) having N-methylhydantoin (NMH) bound thereto in the reaction said NMHASE having a concentration of 3.4 U/ml and 17 U/m; and
 producing a colored response that is substantially proportional to the concentration of creatinine over the normal and at least part of the pathological range; and
 determining said concentration of creatinine in said sample from said colored response without subtracting a blank value associated with a blank reaction.

7. The method of claim 6, wherein said determining is carried out in a dry phase test strip.

8. The method of claim 7, wherein said test strip includes at least two layers.

9. The method of claim 6, further comprising selecting an indicator to minimize color production by the blank reaction.

10. The method of claim 9, wherein the indicator comprises a Trinder pair.

11. The method of claim 10, wherein the Trinder pair is selected from the group consisting of MAOS/MBTH and MAOS/AAP, where MAOS is N-ethyl-N-(2-hydroxy-3-sulfopropyl)-3,5-dimethylaniline, MBTH is 3-methyl-2-benzothiazolineone, and AAP is 4-aminoantipyrine.

12. The method of claim 10, wherein said determining is carried out in a multi-layer dry phase test strip and further wherein the chromogen and oxidative coupler of the Trinder pair are maintained in separate test layers before the sample is tested.

13. The method of claim 6, wherein said using comprises determining the initial concentration of said NMHase in the assay which minimizes interference by the said blank reaction.

* * * * *